United States Patent
Tateishi et al.

(10) Patent No.: US 10,564,232 B2
(45) Date of Patent: Feb. 18, 2020

(54) NUCLEAR SPIN POLARIZATION ENHANCING METHOD THROUGH DYNAMIC NUCLEAR POLARIZATION BY USING SOLUBLE PENTACENE

(71) Applicants: RIKEN, Saitama (JP); OSAKA UNIVERSITY, Osaka (JP)

(72) Inventors: Kenichiro Tateishi, Saitama (JP); Tomohiro Uesaka, Saitama (JP); Makoto Negoro, Osaka (JP); Masahiro Kitagawa, Osaka (JP)

(73) Assignees: Riken, Saitama (JP); Osaka University, Osaka (JP)

( * ) Notice: Subject to any disclaimer, the term of this patent is extended or adjusted under 35 U.S.C. 154(b) by 71 days.

(21) Appl. No.: 15/740,196

(22) PCT Filed: Jun. 27, 2016

(86) PCT No.: PCT/JP2016/069007
§ 371 (c)(1),
(2) Date: Dec. 27, 2017

(87) PCT Pub. No.: WO2017/002761
PCT Pub. Date: Jan. 5, 2017

(65) Prior Publication Data
US 2018/0188338 A1 Jul. 5, 2018

(30) Foreign Application Priority Data
Jun. 29, 2015 (JP) .................................. 2015-129912

(51) Int. Cl.
*G01V 3/00* (2006.01)
*G01R 33/28* (2006.01)
(Continued)

(52) U.S. Cl.
CPC ............ *G01R 33/282* (2013.01); *A61B 5/055* (2013.01); *G01N 24/12* (2013.01); *G01R 33/62* (2013.01)

(58) Field of Classification Search
USPC ......................................................... 324/309
See application file for complete search history.

(56) References Cited

U.S. PATENT DOCUMENTS 7,205,764 B1    4/2007  Anderson et al.
2003/0116755 A1*  6/2003  Takahashi ............... C07C 17/16
                                                          252/500
(Continued)

FOREIGN PATENT DOCUMENTS

JP     2004-503786 A    2/2004
JP     2006-199682 A    8/2006
(Continued)

OTHER PUBLICATIONS

Kagawa et al., "Optimization of 1H spin density for DNP using photo-excited triplet electron spins," The 47th Annual Meeting NMR Society, Japan, 80-83 (2008) (see English abstract).
(Continued)

*Primary Examiner* — Rodney E Fuller
(74) *Attorney, Agent, or Firm* — Morgan, Lewis & Bockius LLP (57) ABSTRACT

An object is to provide a method for enhancing a nuclear spin polarization. Triplet DNP where a pentacene derivative represented by the following formula (A) is used as a polarizing agent enables an effective enhancement in nuclear spin polarization to be achieved. In formula (A), each R independently represents a hydrogen atom (—H), a deuterium atom (-D), or a hydrocarbon group having 1 to 20 carbon atoms which optionally includes at least one atom
(Continued)

selected from the group consisting of an oxygen atom, a sulfur atom and a silicon atom, provided that at least one R represents a hydrocarbon group having 1 to 20 carbon atoms which optionally includes at least one atom selected from the group consisting of an oxygen atom, a sulfur atom and a silicon atom.

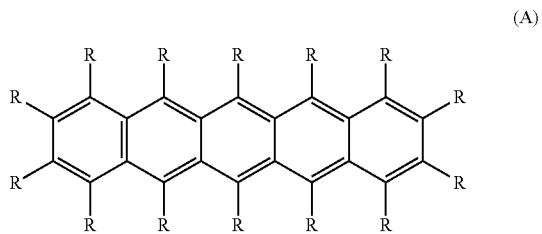

(A)

14 Claims, 3 Drawing Sheets (51) Int. Cl.
*A61B 5/055* (2006.01)
*G01N 24/12* (2006.01)
*G01R 33/62* (2006.01)

(56) References Cited

U.S. PATENT DOCUMENTS

| | | | |
|---|---|---|---|
| 2004/0039281 A1 | 2/2004 | Cook et al. | |
| 2005/0240061 A1* | 10/2005 | Takahashi | C07C 15/38 568/306 |
| 2006/0273311 A1* | 12/2006 | Ohe | H01L 51/0003 257/40 |
| 2007/0222373 A1* | 9/2007 | Arakane | C07C 15/38 313/504 |
| 2008/0241588 A1* | 10/2008 | Hosokawa | C09K 11/06 428/690 |
| 2008/0254319 A1* | 10/2008 | Hosokawa | C07C 15/38 428/704 |
| 2008/0264487 A1* | 10/2008 | Takahashi | B82Y 10/00 136/263 |
| 2012/0048377 A1 | 3/2012 | Winzenberg et al. | |
| 2012/0256630 A1 | 10/2012 | Leussler et al. | |

FOREIGN PATENT DOCUMENTS

| | | |
|---|---|---|
| JP | 2012-519382 A | 8/2012 |
| JP | 2012-220269 A | 11/2012 |
| JP | 2013-516608 A | 5/2013 |

OTHER PUBLICATIONS

International Search Report issued in corresponding International Patent Application No. PCT/JP2016/069007 dated Aug. 16, 2016.
International Preliminary Report on Patentability and Written Opinion issued in corresponding International Patent Application No. PCT/JP2016/069007 dated Jan. 11, 2018.
Extended European Search Report issued in corresponding European Patent Application No. 16817869.7 dated Apr. 26,2019.
Tateishi et al., "Room temperature hyperpolarization of nuclear spins in bulk," Proceedings of the National Academy of Sciences, 111(21): 7527-7530 (2014).
Kaur et al., "Substituent Effects in Pentacenes: Gaining Control over HOMO#LUMO Gaps and Photoxidative Resistances," Journal of the American Chemical Society, 130(48): 16274-16286 (2008).
Pramanik et al., "Water soluble pentacene," Journal of Materials Chemistry C, 1(11): 2193-2201 (2013).
Kawanaka et al., "Using Stable Radicals to Protect Pentacene Derivatives from Photodegradation," Angewandte Chemie International Edition, 52(26): 6643-6647 (2013).
Ito et al., "Excited-State Dynamics of Pentacene Derivatives with Stable Radical Substituents," Angewandte Chemie International Edition, 53 (26): 6715-6719 (2014).
Anonymous, "Pentacene—Wikipedia," Wikipedia, Jan. 28, 2015, retrieved https://en.wikipedia.org/w/index.php?title=Pentacene&oldid= 644588221.
Office Action issued in corresponding Japanese Patent Application No. 2015-129912 dated May 14, 2019.
Kitagawa Lab., Division of Advanced Electronics and Optical Sciences, Systems Innovation, Graduate School of Engineering Science, Osaka University, "Successful exponential increase in NMR signals at room temperature," (research at Osaka University 2014), retrieved http://resou.osaka-u.ac.jp/ja/research/2014/20140513_1 (searched Apr. 19, 2019) (see English abstract).
Chernick et al., "Pentacene Appended to a TEMPO Stable Free Radical: The Effect of Magnetic Exchange Coupling on Photoexcited Pentacene," Journal of the American Chemical Society, 137(2): 857-863 (2015).

* cited by examiner

NUCLEAR SPIN POLARIZATION ENHANCING METHOD THROUGH DYNAMIC NUCLEAR POLARIZATION BY USING SOLUBLE PENTACENE

TECHNICAL FIELD

The present invention relates to a method for enhancing a nuclear spin polarization, more specifically relates to a method for enhancing a nuclear spin polarization by dynamic nuclear polarization using a photoexcited triplet electron of a pentacene derivative.

BACKGROUND ART

Nuclear magnetic resonance (hereinafter, abbreviated as "NMR") is a phenomenon where nuclear spin interacts with an electromagnetic wave in a static magnetic field. A signal intensity of NMR is proportional to a "polarization" representing the degree of nuclear spin alignment. A common polarization, however, is not much more than $10^{-4}$ to $10^{-6}\%$, and it can also be thus said that the signal intensity can be potentially still increased by 10000 times or more.

NMR spectroscopy is one important method in chemical analysis. It, however, is known to be significantly inferior in terms of sensitivity as compared with other analysis methods (such as ultraviolet spectroscopy, infrared spectroscopy, and mass spectrometry). If a low polarization which is one cause of such inferiority can be improved, thereby allowing for measurement of an extremely trace amount of a sample, which has been heretofore difficult to measure in terms of sensitivity.

Also in magnetic resonance imaging (hereinafter, abbreviated as "MRI") widely used in the medical field, a substance enhanced in polarization can also be used as a contrast agent. Such a contrast agent enables an image, which cannot be taken by conventional MRI, such as a metabolic process image, to be taken.

Dynamic nuclear polarization (hereinafter, abbreviated as "DNP") has attracted attention as one solution for an enhancement in polarization, as described in References listed below, and has been actively researched in recent years (see, for example, Patent Documents 1, 2 and 3). DNP is performed according to the following procedures (1) to (3), namely, (1) doping of an electron spin resonance- (hereinafter, abbreviated as "ESR")-active molecule serving as a polarizing agent, with a sample, (2) enhancing of electron spin polarization by a temperature drop or the like, and (3) transferring of the polarization to the nuclear spin by use of a microwave. Thus, electron spin functions to increase the polarization state of nuclear spin, and may be thus referred to as a "polarizing agent". In common DNP, an unpaired electron in a radical is used as a polarizing agent, thereby providing electron spin polarization at 1% or more by use of a low-temperature environment of 100K or less. In NMR signal measurement, however, problems are that [1] a radical molecule causes unnecessary relaxation and/or a reduction in resolution, [2] the maximum gain in principle is 660-fold at most in the case of $^1$H spin, and furthermore [3] an increase in operational cost is caused due to a recent increase in the price of helium, thereby prohibiting widespread use.

Such problems are due to use of a paramagnetic electron in a radical for a polarizing agent, and there is proposed, in order to solve such problems, use of DNP using electron spin at the photoexcited triplet state for a polarizing agent (hereinafter, abbreviated as "triplet DNP"). This electron spin is characterized by not impairing NMR signal measurement because the polarization rate thereof does not depend on the experimental environment and the photoexcited triplet state thereof is rapidly decayed to the ground state after completion of triplet DNP.

The research products by researchers including the present inventor are published in the following URL, and the effectiveness thereof is indicated from the viewpoint that pentacene can achieve a high signal intensity.

http://resou.osaka-u.ac.jp/ja/research/2014/20140513_1

PRIOR ART DOCUMENTS

Patent Documents

[Patent Document 1] JP 2012-220269 A
[Patent Document 2] JP 2013-516608 A
[Patent Document 3] U.S. Pat. No. 7,205,764 B
[Patent Document 4] JP 2004-503786 A

SUMMARY OF THE INVENTION

Technical Problem

As indicated in the research products published in the above URL, pentacene is a potential candidate as a compound which can be used for the polarizing agent of triplet DNP. Pentacene, however, is hardly soluble in most of organic solvents (such as ethanol, acetone, toluene, and chloroform) and is not uniformly dispersed in a solvent, and thus has the problem of being difficult to apply to contrast agents for NMR spectroscopy and MRI.

An object of the present invention is to solve the above problems about triplet DNP, thereby providing a versatile method for enhancing nuclear spin polarization.

Solution to Problem

The present inventors have made intensive studies in order to solve the above problems, and as a result, have found that a specified pentacene derivative is very suitable for triplet DNP. Such a pentacene derivative is soluble in various solvents, and the photoexcited triplet state thereof has a high spin polarization and a proper lifetime.

In triplet DNP, the "pentacene derivative" is irradiated with a laser beam in order to supply electron spin as a polarizing agent. In this regard, the "pentacene derivative" can be called a "polarizing agent" in a broad sense.

That is, the present invention is as follows.
<1> A method for enhancing a nuclear spin polarization by triplet DNP, wherein
a polarizing agent of the triplet DNP is a photoexcited triplet electron of a pentacene derivative represented by the following formula (A) and/or a salt thereof:

(A)

wherein each R independently represents a hydrogen atom (H), a deuterium atom (D), or a hydrocarbon group having 1 to 20 carbon atoms which optionally includes at least one atom selected from the group consisting of an oxygen atom, a sulfur atom and a silicon atom, provided that at least one R represents a hydrocarbon group having 1 to 20 carbon atoms which optionally includes at least one atom selected from the group consisting of an oxygen atom, a sulfur atom and a silicon atom.

<2> The method for enhancing a nuclear spin polarization according to <1>, comprising the following operations (1) to (3):
  (1) preparing a composition including a test compound, the pentacene derivative and/or the salt thereof, and a solvent;
  (2) irradiating the composition prepared in operation (1) with laser in a static magnetic field in order to allow the pentacene derivative and/or the salt thereof to be in a photoexcited triplet state; and
  (3) subjecting the composition, subjected to operation (2) in a magnetostatic field, to magnetic-field sweep and microwave irradiation in order to perform triplet DNP.

<3> The method for enhancing a nuclear spin polarization according to <1> or <2>, which is a method for enhancing a nuclear spin polarization of a subject for NMR spectroscopy measurement.

<4> The method for enhancing a nuclear spin polarization according to <1> or <2>, which is a method for enhancing a nuclear spin polarization of a contrast agent for MRI.

<5> A composition for NMR measurement, including a pentacene derivative represented by the following formula (A) and/or a salt thereof:

(A)

wherein each R independently represents a hydrogen atom (H), a deuterium atom (D), or a hydrocarbon group having 1 to 20 carbon atoms which optionally includes at least one atom selected from the group consisting of an oxygen atom, a sulfur atom and a silicon atom, provided that at least one R represents a hydrocarbon group having 1 to 20 carbon atoms which optionally includes at least one atom selected from the group consisting of an oxygen atom, a sulfur atom and a silicon atom.

Advantageous Effect of the Invention

According to the method of the present invention, there can be achieved an effective enhancement in nuclear spin polarization and an effective increase in sensitivity of NMR spectroscopy. In addition, the composition of the present invention can be used as a contrast agent for MRI.

DESCRIPTION OF THE EMBODIMENTS

The present invention is described in detail with reference to specific examples, but the present invention is not intended to be limited to the following content and can be appropriately modified and carried out without departing from the gist of the present invention.

[Method for Enhancing Nuclear Spin Polarization]

A method for enhancing a nuclear spin polarization (hereinafter, sometimes abbreviated as "the enhancement method of the present invention") according to one aspect of the present invention is a method using triplet DNP, and is characterized in that the polarizing agent is a photoexcited triplet electron of a pentacene derivative represented by the following formula (A) and/or a salt thereof:

(A)

wherein each R independently represents a hydrogen atom (H), a deuterium atom (D), or a hydrocarbon group having 1 to 20 carbon atoms which optionally includes at least one atom selected from the group consisting of an oxygen atom, a sulfur atom and a silicon atom, provided that at least one R represents a hydrocarbon group having 1 to 20 carbon atoms which optionally includes at least one atom selected from the group consisting of an oxygen atom, a sulfur atom and a silicon atom.

As described above, pentacene is a potential candidate as a compound which can be used for the polarizing agent of triplet DNP, but pentacene is hardly soluble in most of organic solvents (such as ethanol, acetone, toluene, and chloroform). Therefore, a problem is that pentacene is hardly dispersed in a solvent and thus cannot be practically applied to versatile contrast agents for NMR spectroscopy and MRI.

The present inventors have found that a pentacene derivative represented by formula (A) is very suitable for triplet DNP because the pentacene derivative is soluble in various solvents and furthermore the photoexcited triplet electron thereof has a high spin polarization and a proper lifetime.

In the measurement method of the present invention, electron spin polarization of the photoexcited triplet electron of the pentacene derivative represented by formula (A) is transferred to nuclear spin in a component material in a propagative manner and an NMR signal increased in nuclear spin polarization is measured. The pentacene derivative represented by formula (A) is soluble in various solvents, and the photoexcited triplet electron thereof has a high spin polarization, thereby enabling an effective enhancement in nuclear spin polarization to be achieved.

Hereinafter, the "pentacene derivative represented by formula (A)" will be described in detail.

<Pentacene Derivative Represented by Formula (A)>

While the enhancement method of the present invention is characterized in that the polarizing agent of triplet DNP is a photoexcited triplet electron of a pentacene derivative represented by the following formula (A) and/or a salt thereof, specific types of the pentacene derivative and the salt are not particularly limited and can be appropriately selected for any purpose.

(A)

In formula (A), each R independently represents a hydrogen atom (H), a deuterium atom (D), or a hydrocarbon group having 1 to 20 carbon atoms which optionally includes at least one atom selected from the group consisting of an oxygen atom, a sulfur atom and a silicon atom, provided that at least one R represents a hydrocarbon group having 1 to 20 carbon atoms which optionally includes at least one atom selected from the group consisting of an oxygen atom, a sulfur atom and a silicon atom.

In formula (A), while each R independently represents a hydrogen atom (H), a deuterium atom (D), or a hydrocarbon group having 1 to 20 carbon atoms which optionally includes at least one atom selected from the group consisting of an oxygen atom, a sulfur atom and a silicon atom, it is meant that the "hydrocarbon group" is not limited to a linear saturated hydrocarbon group and may include each of a carbon-carbon unsaturated bond, a branched structure and a cyclic structure. In addition, the phrase "which optionally includes at least one atom selected from the group consisting of an oxygen atom, a sulfur atom and a silicon atom" means that not only a functional group including an oxygen atom, a sulfur atom or a silicon atom may be included, but also a linking group including an oxygen atom, a sulfur atom or a silicon atom may be included in the interior or at the terminal of the carbon backbone. Accordingly, examples of the hydrocarbon group "which optionally includes at least one atom selected from the group consisting of an oxygen atom, a sulfur atom and a silicon atom" include a hydrocarbon group containing a hydroxyl group and having two carbon atoms, such as —$CH_2$—$CH_2$—OH, a hydrocarbon group containing an ether group in the interior of the carbon backbone and having two carbon atoms, such as —$CH_2$—O—$CH_3$, and a hydrocarbon group containing an ether group at the terminal of the carbon backbone and having two carbon atoms, such as —O—$CH_2$—$CH_3$.

The "salt" of the pentacene derivative is a compound where the pentacene derivative has an acid point such as a carboxyl group (—COOH) or a sulfo group (—$SO_3H$) and where the hydrogen ion is replaced with a metal cation.

The phrase "at least one R represents a hydrocarbon group having 1 to 20 carbon atoms which optionally includes at least one atom selected from the group consisting of an oxygen atom, a sulfur atom and a silicon atom" means, namely, that the pentacene derivative represented by formula (A) does not encompass pentacene by itself and deuterated pentacene.

When R represents a hydrocarbon group, the number of carbon atoms in the hydrocarbon group is preferably 3 or more, more preferably 6 or more, and preferably 12 or less, more preferably 8 or less.

Examples of the hydrocarbon group include a phenyl group, a biphenyl group, a phenylthio group, a decylthio group and an ethynyl group.

Examples of the functional group and the linking group included in the hydrocarbon group include a carboxyl group (—COOH), a potassium salt (—COOK) of a carboxyl group, a thioether group (—S—), a triethylsilyl group (—$SiEt_3$), and a triisopropylsilyl group (—$SiPr_3$).

The number of bond(s) in the hydrocarbon group is usually 1 or more, preferably 2 or more, and usually 6 or less, preferably 5 or less.

Examples of the binding position(s) in the hydrocarbon group include a combination of the 6-position and the 13-position (the number of bonds in the hydrocarbon group: 2), a combination of the 5-position, the 7-position, the 12-position and the 14-position (the number of bonds in the hydrocarbon group: 4), a combination of the 1-position, the 4-position, the 8-position and the 11-position (the number of bonds in the hydrocarbon group: 4), and a combination of the 2-position, the 3-position, the 9-position and the 10-position (the number of bonds in the hydrocarbon group: 4), and most preferable is a combination of the 6-position and the 13-position. A combination of the 5-position, the 7-position, the 12-position and the 14-position, a combination of the 1-position, the 4-position, the 8-position and the 11-position, and a combination of the 2-position, the 3-position, the 9-position and the 10-position are preferable in this order. While the pentacene derivative tends to be easily oxidized and decomposed when dissolved in a solvent in the air, the decomposition speed is slower in the above order depending on the position at which the hydrocarbon group is added. This order corresponds to the descending order of the spin density of the π-electron cloud of pentacene.

In addition, Proc. Natl. Acad. Sci, U.S.A. 2014, 111, 7527-7530 indicates that a hydrogen atom included in pentacene is substituted with a deuterium atom, thereby resulting in an enhancement in the $^1H$ spin polarization achieved by triplet DNP.

Examples of the pentacene derivative represented by formula (A) and/or the salt thereof include:

1: 6,13-diphenylpentacene,
2: 6,13-bis(2',6'-dimethylphenyl)pentacene,
3: 6,13-bis(2',6'-diethylphenyl)pentacene,
4: 6,13-dibiphenylpentacene,
5: 3,3'-(6,13-pentacenediyldisulfanediyl)dipropionic acid,
6: potassium 3,3'-(6,13-pentacenediyldisulfanediyl)dipropionate,
7: 6,13-bis(n-decylthio)pentacene,
8: 6,13-bis(phenylthio)pentacene,
9: 6,13-bis[(triethylsilyl)ethynyl]pentacene, and
10: 6,13-bis[(triisopropylsilyl)ethynyl]pentacene (see the following formulae).

1

2

3

4

5

6

7

Among the above, pentacene derivative 1, pentacene derivative 4, pentacene derivative 9 and pentacene derivative 10 are subjected to ESR evaluation and NMR measurement in Examples.

In addition, J. Am. Chem. Soc. 2008, 130, 16274-16286 specifically describes, for example, the effect of a substituent on a HOMO-LUMO gap and photooxidation resistance of pentacenes with respect to each of pentacene derivative 1, pentacene derivative 2, pentacene derivative 7, pentacene derivative 8 and pentacene derivative 10.

Furthermore, J. Master. Chem. C, 2013, 1, 2193-2201 describes pentacene derivatives such as pentacene derivative 5 and pentacene derivative 6 being soluble in water, and it is also clear that the pentacene derivative represented by formula (A) and/or the salt thereof can be combined with a solvent and thus dissolved therein, and can be used as the polarizing agent of triplet DNP.

The above ten types of chemical formulae also encompass those where a hydrogen atom (H) included in each chemical formula is partially or fully substituted with a deuterium atom (D).

The application of the enhancement method of the present invention is not particularly limited, and examples thereof include applications to contrast agents for NMR spectroscopy and MRI.

While the enhancement method of the present invention is a method for enhancing a nuclear spin polarization by triplet DNP, an operation for performing triplet DNP, an operation for measuring an NMR signal, and the like are not particularly limited and can be appropriately selected from known contents for any purpose.

Specific operations included in the measurement method of the present invention include the following operations (1) to (3):

(1) preparing a composition including a test (research object) compound, the pentacene derivative and/or the salt thereof, and a solvent;

(2) irradiating the composition prepared in operation (1) with laser in a magnetostatic field in order to allow the pentacene derivative and/or the salt thereof to be in a photoexcited triplet state; and (3) subjecting the composition, subjected to operation (2) in a magnetostatic field, to magnetic-field sweep and microwave irradiation in order to perform triplet DNP.

Hereinafter, "operations (1) to (3)" will be described in detail.

<Operation (1)>

Operation (1) is an operation for preparing a composition including a test compound, a pentacene derivative represented by formula (A) and/or a salt thereof, and a solvent, and the content of the pentacene derivative represented by formula (A) in the composition, a specific type of the solvent and the content thereof in the composition, and the like are not particularly limited and can be appropriately selected for any purpose. Hereinafter, the detail will be described with reference to specific examples.

The content of the pentacene derivative represented by formula (A) in the composition is usually 0.01 mM or more, preferably 0.1 mM or more, more preferably 1 mM or more, and usually 100 mM or less, preferably 50 mM or less, more preferably 10 mM or less. When the content falls within the range, the nuclear spin polarization is easily increased.

Examples of the solvent include benzene, toluene, water, methanol, ethanol, dichloromethane, chloroform, N,N-dimethylformamide (DMF), dimethylsulfoxide (DMSO), ethylene glycol, glycerin, polystyrene, deuterated benzene (benzene-$d_6$), deuterated toluene (toluene-$d_8$), deuterated water (water-$d_1$), deuterated methanol (methanol-$d_4$), deuterated ethanol (ethanol-$d_6$), deuterated dichloromethane (dichloromethane-$d_2$), deuterated chloroform (dichloromethane-$d_1$), deuterated N,N-dimethylformamide (DMF-$d_7$), deuterated dimethylsulfoxide (DMSO-$d_6$), deuterated ethylene glycol (ethylene glycol-$d_6$), deuterated glycerin (glycerin$d_8$), deuterated polystyrene, or mixed liquids of two or more thereof.

While a solvent that can dissolve the test compound and the pentacene derivative is desirably used in terms of uniform dispersion, the test compound is not necessarily dissolved in a solvent, and is considered to be able to be expected to exert a significant effect even when being merely in contact with a solvent in moderation in which the pentacene derivative is dissolved.

When the test compound is a substance having a large void, like a nanocrystal or zeolite, the solvent in which the pentacene derivative is dissolved enters the void. When the test compound is a flexible substance like a polymer, rubber or a cell wall, the solvent in which the pentacene derivative is dissolved penetrates into or swells the test compound.

Thus, it is considered that the corresponding effects to the dimension attribution, the hardness (elasticity) attribution and the like depending on the type of the test compound can be expected.

The content of the solvent in the composition in NMR spectroscopy is usually 50% by mass or more, preferably 90% by mass or more, more preferably 99% by mass or more, and usually 99.999% by mass or less, preferably 99.99% by mass or less, more preferably 99.9% by mass or less. When the content falls within the range, the nuclear spin polarization is easily increased.

The content of the solvent in the composition in the application of a contrast agent for MRI is usually 30% by mass or more, preferably 50% by mass or more, more preferably 70% by mass or more, and usually 99.9% by mass or less, preferably 99% by mass or less, more preferably 90% by mass or less.

The content of the test compound in the composition in NMR spectroscopy is usually 0.001% by mass or more, preferably 0.01% by mass or more, more preferably 0.1% by mass or more, and usually 30% by mass or less, preferably 10% by mass or less, more preferably 3% by mass or less. When the content falls within the range, the nuclear spin polarization is easily increased.

The content of the test compound in the composition in the application of a contrast agent for MRI is usually 3% by mass or more, preferably 10% by mass or more, more preferably 20% by mass or more, and usually 90% by mass or less, preferably 70% by mass or less, more preferably 50% by mass or less.

When the test compound in NMR spectroscopy is a protein, the content ratio of the test compound to an aqueous solvent (Mass of test compound/Mass of solvent) is usually 0.0001% or more, preferably 0.001% or more, more preferably 0.01% or more, and usually 10% or less, preferably 5% or less, more preferably 1% or less.

When the test compound in the application of a contrast agent for MRI is pyruvic acid, the content ratio of the test compound to an aqueous solvent (Mass of test compound/Mass of solvent) is usually 1% or more, preferably 5% or more, more preferably 10% or more, and usually 90% or less, preferably 70% or less, more preferably 50% or less.

<Operation (2)>

Operation (2) is an operation for irradiating the composition prepared in (1) with laser in a magnetostatic field in order to allow the pentacene derivative to be in a photoexcited triplet state, and the magnetic flux density of the magnetostatic field, and the wavelength, the intensity and the like of the laser should be appropriately selected depending on the type and the content of the pentacene derivative represented by formula (A) and are not particularly limited. Hereinafter, the detail will be described with reference to specific examples.

The magnetic flux density of the magnetostatic field is usually 0.01 T or more, preferably 0.1 T or more, more preferably 0.3 T or more, and usually 30 T or less, preferably 5 T or less, more preferably 1 T or less.

The wavelength of the laser is usually 500 nm or more, preferably 550 nm or more, more preferably 590 nm or more, and usually 700 nm or less, preferably 670 nm or less, more preferably 650 nm or less. Herein, the wavelength in the case of use of 6,13-diphenylpentacene, 6,13-dibiphenylpentacene or the like is, for example, 589 nm.

The laser intensity is usually 10 mW or more, preferably 100 mW or more, more preferably 1 W or more, and usually 50 W or less, preferably 30 W or less, more preferably 10 W or less. When the laser intensity falls within the range, the pentacene derivative can be sufficiently excited.

The laser may be any of continuous wave laser and pulse oscillation laser, and is preferably pulse oscillation laser.

When the laser is pulse oscillation laser, examples of the waveform thereof include a Gaussian waveform, a rectangular waveform and a triangular waveform, and a rectangular waveform is preferable.

When the laser is pulse oscillation laser, the pulse width is usually 1 ns or more, preferably 10 ns or more, more preferably 100 ns or more, and usually 100 μs or less, preferably 30 μs or less, more preferably 10 μs or less.

When the laser is pulse oscillation laser, the pulse period is usually 10 Hz or more, preferably 50 Hz or more, more preferably 100 Hz or more, and usually 10 kHz or less, preferably 3 kHz or less, more preferably 1 kHz or less.

When the laser is pulse oscillation laser, the pulse number is usually 1,000 or more, preferably 10,000 or more, more preferably 50,000 or more, and usually 1,000,000 or less, preferably 500,000 or less, more preferably 300,000 or less.

When the number falls within the range, the pentacene derivative can be sufficiently excited.

The apparatus for performing laser irradiation is not particularly limited, and examples thereof include an apparatus where two laser beams different in wavelength are superimposed in a nonlinear optical crystal to perform sum frequency generation (SFG). For example, a YAG laser beam at 1064 nm and a YAG laser beam at 1319 nm can be superimposed in a nonlinear optical crystal $LiB_3O_5$, thereby resulting in conversion to a beam at 589 nm.

Other conditions in operation (2) are not particularly limited, and operation (2) is preferably performed in the state where the composition is cooled to a temperature equal to or less than the glass transition temperature. In the state where the composition is cooled, an advantage is that the retention time of nuclear spin produced, in a high polarization state, is elongated.

While a lower temperature of the composition in operation (2) is more desirable, the temperature of the composition is usually room temperature, preferably a temperature equal to or less than the melting point of the solvent, more preferably a temperature equal to or less than the glass transition temperature of the solvent.

When the solvent is ethanol, the melting point is 160K and the glass transition temperature is 100K.

When the solvent is toluene, the melting point is 178K and the glass transition temperature is 115K.

<Operation (3)>

Operation (3) is an operation for performing magnetic-field sweep and microwave irradiation of the composition subjected to operation (2) in a magnetostatic field in order to perform triplet DNP. The magnetic flux density of the magnetostatic field, the wavelength of the microwave, the magnetic-field sweep speed, and the like should be appropriately selected depending on the type and the like of a nucleus to be measured, and are not particularly limited. Hereinafter, the detail will be described with reference to specific examples.

The magnetic flux density of the magnetostatic field is usually the same as the magnetic flux density in operation (2).

The apparatus for performing magnetic-field sweep and microwave irradiation is not particularly limited, and examples thereof include a magnetic-field sweeping apparatus, a microwave oscillator, a microwave resonator and a microwave switch.

The microwave may be any of a continuous microwave and a pulse oscillation microwave, and is preferably a pulse oscillation microwave. Herein, the magnetic-field sweep and the microwave irradiation are in synchronization with and usually performed at the same time as laser irradiation.

The frequency of the microwave is usually 100 MHz or more, preferably 1 GHz or more, more preferably 8 GHz or more, and usually 1 THz or less, preferably 100 GHz or less, more preferably 30 GHz or less.

When a pulse oscillation microwave is used, examples of the waveform of a magnetic field swept include a triangular waveform, a sinusoidal waveform and a saw-tooth waveform, and a triangular waveform is preferable.

When a pulse oscillation microwave is used, examples of the form of the microwave for irradiation include a rectangular waveform, a triangular waveform and a saw-tooth waveform, and a rectangular waveform is preferable.

When a pulse oscillation microwave is used, the pulse width of each of the magnetic field and the microwave is usually 1 µs or more, preferably 5 µs or more, more preferably 10 µs or more, and usually 1 ms or less, preferably 100 µs or less, more preferably 50 µs or less.

When the width falls within the range, a high signal intensity is easily achieved.

The magnetic-field sweeping width is usually 0.1 mT or more, preferably 1 mT or more, more preferably 10 mT or more, and usually 1 T or less, preferably 500 mT or less, more preferably 100 mT or less.

Other conditions in operation (3) not particularly limited, and operation (3) is preferably performed in the state where the composition is cooled to a temperature equal to or less than the glass transition temperature. In the state where the composition is cooled, an advantage is that the retention time of nuclear spin produced, in a high polarization state, is elongated.

While a lower temperature of the composition in operation (3) is more desirable, the temperature of the composition is usually room temperature, preferably a temperature equal to or less than the melting point of the solvent, more preferably a temperature equal to or less than the glass transition temperature of the solvent.

When the solvent is ethanol, the melting point is 160K and the glass transition temperature is 100K.

When the solvent is toluene, the melting point is 178K and the glass transition temperature is 115K.

The following operation (4) generally follows operation (3).

<Operation (4)>

The enhancement method of the present invention can be used in a measurement method of an NMR signal, such as NMR spectroscopy as a chemical analysis application, a contrast agent for MRI or the like, as described above. When the enhancement method of the present invention is used in such applications, examples of the measurement method of an NMR signal include a method including the following operation (4):

Operation (4) for measuring an NMR signal of the test compound in a magnetostatic field by use of the composition subjected to operation (3).

Operation (4) is an operation for measuring an NMR signal of the test compound in a magnetostatic field by use of the composition subjected to operation (3), and the apparatus for measurement of an NMR signal, and the like should be appropriately selected depending on a continuous wave method, a pulse-Fourier transform method and the like, and are not particularly limited. When a pulse-Fourier transform method is used, examples of the apparatus include an apparatus including an RF coil (probe), an amplifier, and the like.

[Composition for NMR Signal Measurement]

The pentacene derivative represented by formula (A) and/or the salt thereof is very suitable for a triplet DNP method, as described above. One aspect of the present invention also provides a composition for NMR signal measurement including a pentacene derivative represented by the following formula (A) and/or a salt thereof. Herein, specific types of the pentacene derivative represented by formula (A) and/or the salt thereof in the composition for NMR signal measurement are/is the same as described in [Method for enhancing nuclear spin polarization].

(A)

In formula (A), each R independently represents a hydrogen atom (H), a deuterium atom (D), or a hydrocarbon group having 1 to 20 carbon atoms which optionally includes at least one atom selected from the group consisting of an oxygen atom, a sulfur atom and a silicon atom, provided that at least one R represents a hydrocarbon group having 1 to 20 carbon atoms which optionally includes at least one atom selected from the group consisting of an oxygen atom, a sulfur atom and a silicon atom.

EXAMPLES

Hereinafter, the present invention will be further specifically described with reference to Examples, but the present invention can be appropriately modified without departing from the gist thereof. Accordingly, the scope of the present invention should not be construed limitedly by specific examples indicated below.

Herein, all samples are compositions containing no test compound and including the pentacene derivative and/or the salt thereof and the solvent. As long as triplet DNP is carried out, the nuclear spins included in such three components are equally highly polarized. Therefore, the presence of the test compound is not necessarily essential in order to exhibit the practicability of triplet DNP. In Examples, conducted were a confirmation of dissolution of the pentacene derivative and/or the salt thereof in the solvent, a confirmation of production of a photoexcited triplet electron with ESR measurement, and a confirmation of an increase in NMR signal intensity of $^1H$ spin in the solvent by triplet DNP.

Preparation of Composition for NMR Signal Measurement

Example 1

6,13-Diphenylpentacene (0.4 mg, produced by Sigma-Aldrich Co., Ltd.) represented by the following formula was prepared as the pentacene derivative represented by formula (A), and dissolved in a mixed liquid of water and deuterated ethanol (2 mL, pure water:ethanol=1:9% by mass) as the solvent, thereby preparing a sample. It was here confirmed that 6,13-diphenylpentacene in the composition was completely dissolved.

Example 2

6,13-Diphenylpentacene (0.5 mg) represented by the above formula, as the pentacene derivative represented by formula (A), was dissolved in a mixed liquid of benzene and polystyrene (1 mL, benzene:polystyrene=5:5% by mass) as the solvent, thereby preparing a sample. It was here confirmed that 6,13-diphenylpentacene in the composition was completely dissolved.

Example 3

6,13-Diphenylpentacene (0.5 mg) represented by the above formula, as the pentacene derivative represented by formula (A), was dissolved in a mixed liquid of benzene and deuterated toluene (1 mL, benzene:deuterated toluene=1:9% by mass) as the solvent, thereby preparing a sample. It was here confirmed that 6,13-diphenylpentacene in the composition was completely dissolved.

Example 4

6,13-Dibiphenylpentacene (0.4 mg, produced by Luminescence Technology Crop.) represented by the following formula, as the pentacene derivative represented by formula (A), was dissolved in a mixed liquid of benzene and deuterated toluene (2 mL, benzene:deuterated toluene=1:9% by mass) as the solvent, thereby preparing a sample. It was here confirmed that 6,13-dibiphenylpentacene in the composition was completely dissolved.

Example 5

6,13-Bis[(triethylsilyl)ethynyl]pentacene (0.4 mg, produced by Sigma-Aldrich Co., Ltd.) represented by the following formula, as the pentacene derivative represented by formula (A), was dissolved in a mixed liquid of benzene and polystyrene (2 mL, benzene:polystyrene=5:5% by mass) as the solvent, thereby preparing a sample. It was here confirmed that 6,13-bis[(triethylsilyl)ethynyl]pentacene in the composition was completely dissolved.

Example 6

6,13-Bis[(triisopropylsilyl)ethynyl]pentacene (0.4 mg, produced by Tokyo Chemical Industry Co., Ltd.) represented by the following formula, as the pentacene derivative represented by formula (A), was dissolved in a mixed liquid of benzene and polystyrene (2 mL, benzene:polystyrene=5:5% by mass) as the solvent, thereby preparing a sample. It was here confirmed that 6,13-bis[(triisopropylsilyl)ethynyl]pentacene in the composition was completely dissolved.

Comparative Example

Pentacene (0.4 mg, produced by Sigma-Aldrich Co., Ltd.) represented by the following formula, and a mixed liquid of benzene and deuterated toluene (2 mL, benzene:deuterated toluene=1:9% by mass) as the solvent were mixed, thereby preparing a composition for NMR measurement. The pentacene in the composition, however, was not almost dissolved, and deposited on the bottom of the vessel.

<Evaluation of Triplet Electron of Pentacene Derivative by ESR>

The composition prepared in each of Examples 1 to 6 was loaded in a sample tube (material: Pyrex (registered trademark)), cooled to 100K or less and thus formed into a glassy composition, and the electron spin resonance of the triplet electron of each pentacene derivative was evaluated.

Figure 1:
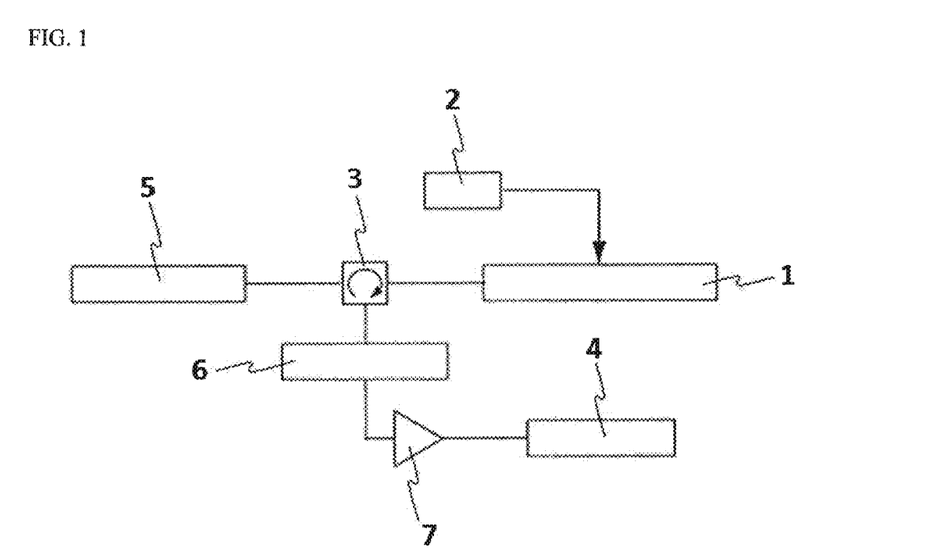
FIG. 1 illustrates a schematic view of an ESR evaluation apparatus used in Examples.

Herein, the evaluation apparatus of the electron spin resonance had a configuration illustrated in the schematic view of FIG. 1. For generation of laser, a system was used where a YAG laser beam at 1064 nm and a YAG laser beam at 1319 nm were superimposed in a nonlinear optical crystal $LiB_3O_5$, thereby resulting in conversion to a beam at 589 nm. A dielectric resonator was used as the microwave resonator, and the resonance frequency was set to 18 GHz. The resonator had a cylindrical shape for loading of the sample tube, and further included an optical window for laser irradiation and a cooling gas inlet.

The signal of the electron spin resonance was measured by a Q-meter method. More specifically, such measurement was made by allowing a microwave having a resonance frequency corresponding to the resonance frequency of the resonator to continuously enter from a microwave oscillator, transducing the resulting reflected wave to a DC wave by a diode detector, and monitoring the DC wave by an oscilloscope. This is based on a mechanism where laser irradiation produces electron spin and the impedance of the resonator is changed, resulting in the change in reflected wave.

Figure 2:
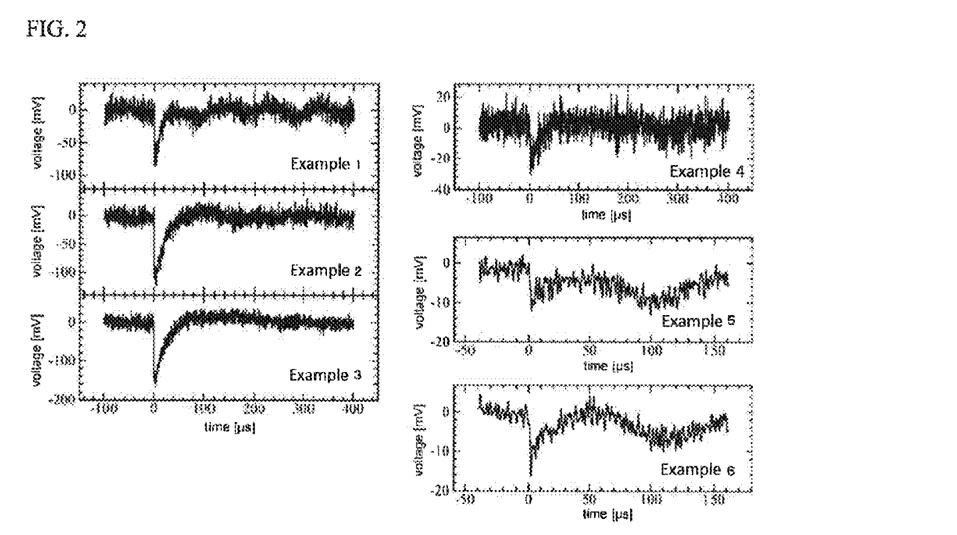
FIG. 2 represents the measurement results of ESR signals of compositions in Examples 1 to 6.

The measurement results are represented in FIG. 2.

It was revealed from the measurement results in FIG. 2 that the composition in each of Examples 1 to 6 enabled the signal of the reflected wave derived from the pentacene derivative to be confirmed and the composition was available in a triplet DNP method. Herein, while the damping time constant of the signal of the reflected wave derived from the pentacene derivative was significantly changed depending on the solvent, such change was considered to have no large effect on use in a triplet DNP method.

<NMR Measurement>

The composition prepared in each of Examples 1 to 6 was loaded in a sample tube, cooled to 100K or less and thus formed into a glassy composition, and subjected to triplet DNP and thereafter NMR measurement.

Figure 3:
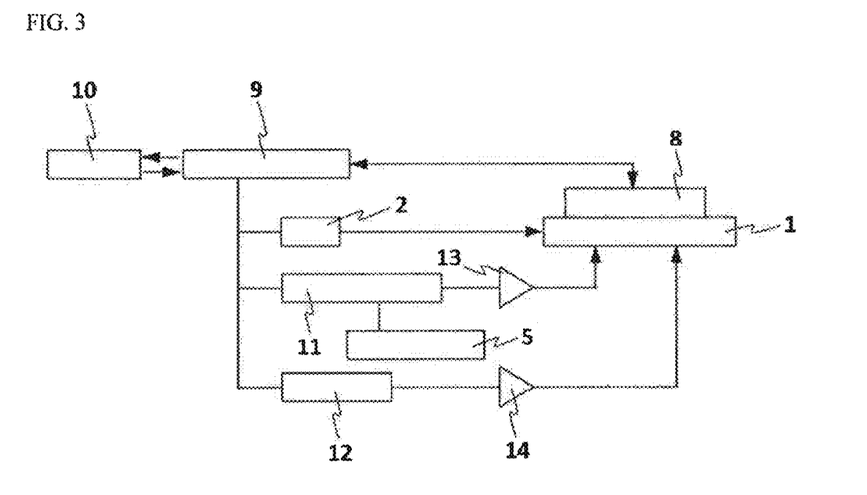
FIG. 3 illustrates a schematic view depicting a system of an NMR measurement apparatus used in Examples.
Figure 4:
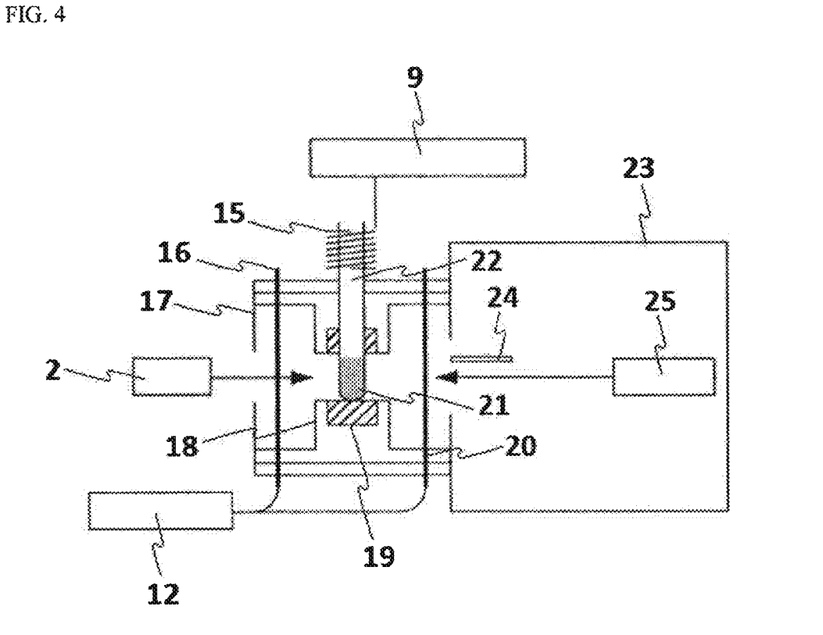
FIG. 4 illustrates a schematic view depicting a configuration of the NMR measurement apparatus used in Examples.

The measurement apparatus of triplet DNP had a configuration illustrated in schematic views of FIGS. 3 and 4, and specifically included a laser oscillator, a microwave oscillator, a microwave resonator, a microwave switch and a magnetic-field sweeping apparatus.

Figure 5:
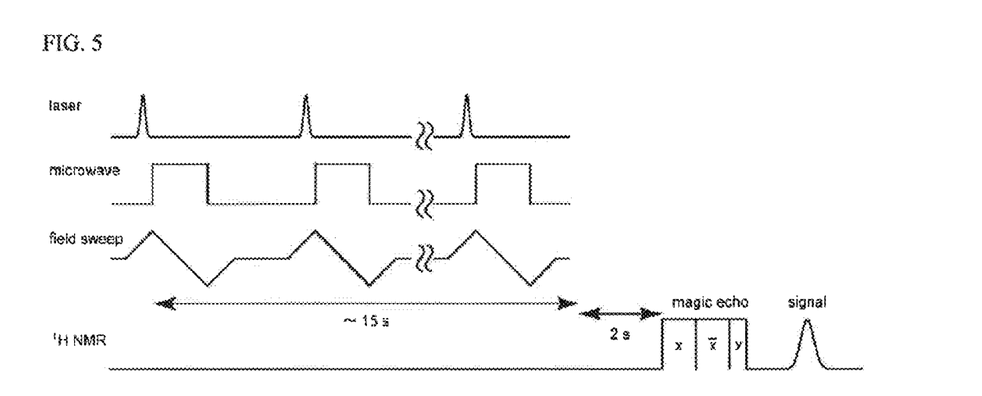
FIG. 5 illustrates a sequence including laser irradiation, magnetic-field sweep and microwave irradiation performed in Examples.

Laser irradiation, magnetic-field sweep, microwave irradiation and NMR detection were performed according to a sequence illustrated in FIG. 5. More specifically, such a sequence was repeated with controlling the timing of the laser pulse, the microwave converted into a pulse by switching, and magnetic field sweep of a triangular wave. Thereafter, the sample tube was transferred to a coil for NMR detection, and the NMR signal (magic echo sequence) of $^1H$ spin was measured.

Figure 6:
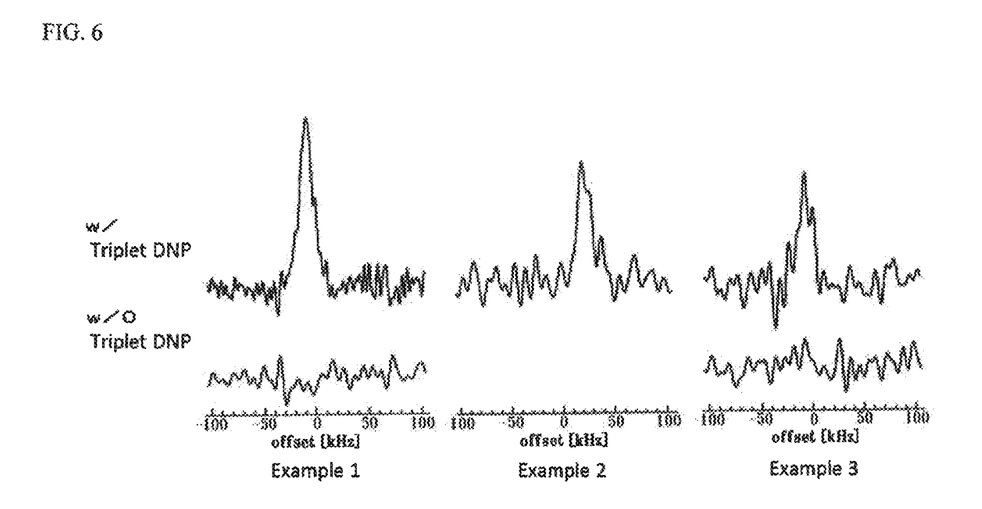
FIG. 6 represents the measurement results of NMR signals of $^1H$ spins of compositions in Examples 1 to 3.

Laser (Pulse Oscillation)
Waveform: Gaussian waveform
Pulse width: 126 ns
Pulse period: 200 Hz
Pulse number: 3,000
Microwave (Pulse Oscillation)
Waveform: rectangular waveform
Pulse width: 20 μs
Pulse period: 200 Hz
Pulse number: 3,000
Magnetic Field Swept (Pulse Oscillation)
Waveform: triangular waveform
Pulse width: 20 μs
Pulse period: 200 Hz
Pulse number: 3,000
Other Conditions
Magnetostatic field: 0.65 T
Temperature: 100K The measurement results are represented in FIG. 6. There is also represented the result of the signal of $^1H$ spin in the case of no triplet DNP performed as a reference.

It was revealed from the measurement results of FIG. 6 that a signal increased in polarization of nuclear spin was obtained from the composition in each of Examples 1 to 3.

INDUSTRIAL APPLICABILITY

The enhancement method of the present invention can be used not only in NMR spectroscopy for identification and structure determination of an organic compound and the like, but also as a method for enhancing a nuclear spin polarization of a contrast agent for MRI.

It is noted that the content of the basic application and the contents of Cited References (Patent Documents) are herein incorporated.

REFERENCE SIGNS LIST 1 microwave resonator
2 laser oscillator
3 circulator
4 oscilloscope
5 local oscillator 6 diode detector
7 operational amplifier
8 NMR resonator
9 NMR spectrometer
10 computer
11 microwave switch
12 magnetic-field sweeping apparatus
13 microwave amplifier
14 operational amplifier
15 coil for NMR detection
16 enclosure (copper)
17 enclosure (brass)
18 resonator holder (Teflon (registered trademark))
19 cylindrical dielectric resonator
20 coil for magnetic field sweep
21 composition
22 sample tube
23 waveguide
24 Gordon coupler
25 microwave oscillator

The invention claimed is:

1. A method for enhancing a nuclear spin polarization by triplet DNP, comprising
performing triplet DNP using a photoexcited triplet electron of a pentacene derivative represented by the following formula (A) and/or a salt thereof, as a polarization source of triplet DNP:

(A)

wherein each R independently represents a hydrogen atom (H), a deuterium atom (D), or a hydrocarbon group having 1 to 20 carbon atoms which optionally includes at least one atom selected from the group consisting of an oxygen atom, a sulfur atom and a silicon atom, provided that at least one R represents a hydrocarbon group having 1 to 20 carbon atoms which optionally includes at least one atom selected from the group consisting of an oxygen atom, a sulfur atom and a silicon atom.

2. The method for enhancing a nuclear spin polarization according to claim 1, comprising the following operations (1) to (3):
(1) preparing a composition including a test compound, the pentacene derivative and/or the salt thereof, and a solvent;
(2) irradiating the composition prepared in operation (1) with laser in a magnetostatic field in order to allow the pentacene derivative and/or the salt thereof to be in a photoexcited triplet state; and
(3) subjecting the composition, subjected to operation (2) in a magnetostatic field, to magnetic-field sweep and microwave irradiation in order to perform triplet DNP.

3. The method for enhancing a nuclear spin polarization according to claim 1, comprising enhancing a nuclear spin polarization of a subject for chemical analysis measurement.

4. The method for enhancing a nuclear spin polarization according to claim 1, comprising enhancing a nuclear spin polarization of a contrast agent for MRI.

5. The method for enhancing a nuclear spin polarization according to claim 1, wherein the formula (A) is 6,13-Diphenylpentacene.

6. The method for enhancing a nuclear spin polarization according to claim 1, wherein the formula (A) is 6,13-Dibiphenylpentacene.

7. The method for enhancing a nuclear spin polarization according to claim 1, wherein the formula (A) is 6,13-Bis[(triethylsilyl)ethynyl]pentacene.

8. The method for enhancing a nuclear spin polarization according to claim 1, wherein the formula (A) is 6,13-Bis[(triisopropylsilyl)ethynyl]pentacene.

9. The method for enhancing a nuclear spin polarization according to claim 1, wherein the formula (A) is selected from the group consisting of 6,13-bis(2',6'-dimethylphenyl)pentacene, 6,13-bis(2',6'-diethylphenyl)pentacene, 3,3'-(6,13-pentacenediyldisulfanediyl)dipropionic acid, potassium 3,3'-(6,13-pentacenediyldisulfanediyl)dipropionate, 6,13-bis(n-decylthio)pentacene, and 6,13-bis(phenylthio)pentacene.

10. The method for enhancing a nuclear spin polarization according to claim 1, wherein at least one R represents a hydrocarbon group having 1 to 20 carbon atoms which includes an oxygen atom.

11. The method for enhancing a nuclear spin polarization according to claim 1, wherein at least one R represents a hydrocarbon group having 1 to 20 carbon atoms which includes a sulfur atom.

12. The method for enhancing a nuclear spin polarization according to claim 1, wherein at least one R represents a hydrocarbon group having 1 to 20 carbon atoms which includes a silicon atom.

13. A method for NMR measurement, comprising
performing triplet DNP using a photoexcited triplet electron of a pentacene derivative represented by the following formula (A) and/or a salt thereof, as a polarization source of triplet DNP:

(A)

wherein each R independently represents a hydrogen atom (H), a deuterium atom (D), or a hydrocarbon group having 1 to 20 carbon atoms which optionally includes at least one atom selected from the group consisting of an oxygen atom, a sulfur atom and a silicon atom, provided that at least one R represents a hydrocarbon group having 1 to 20 carbon atoms which optionally includes at least one atom selected from the group consisting of an oxygen atom, a sulfur atom and a silicon atom, and
performing NMR measurement.

14. A method for measuring NMR of a sample, comprising
performing triplet DNP using a photoexcited triplet electron of a pentacene derivative represented by the following formula (A) and/or a salt thereof, as a polarization source of triplet DNP:

wherein each R independently represents a hydrogen atom (H), a deuterium atom (D), or a hydrocarbon group having 1 to 20 carbon atoms which optionally includes at least one atom selected from the group consisting of an oxygen atom, a sulfur atom and a silicon atom, provided that at least one R represents a hydrocarbon group having 1 to 20 carbon atoms which optionally includes at least one atom selected from the group consisting of an oxygen atom, a sulfur atom and a silicon atom, and performing NMR measurement on the sample other than the pentacene derivative.

* * * * *